(12) United States Patent
Christy et al.

(10) Patent No.: US 8,512,259 B2
(45) Date of Patent: Aug. 20, 2013

(54) TACTILE SENSORY TESTING INSTRUMENT

(75) Inventors: George Michael Christy, Lincoln, CA (US); Jacob Stuart Duane, Roseville, CA (US)

(73) Assignee: George Michael Christy, Lincoln, CA (US)

( * ) Notice: Subject to any disclaimer, the term of this patent is extended or adjusted under 35 U.S.C. 154(b) by 732 days.

(21) Appl. No.: 12/782,712

(22) Filed: May 19, 2010

(65) Prior Publication Data
US 2011/0288434 A1    Nov. 24, 2011

(51) Int. Cl.
*A61B 19/00* (2006.01)
(52) U.S. Cl.
USPC .......................................................... 600/557
(58) Field of Classification Search
USPC .......................................................... 600/557
See application file for complete search history.

(56) References Cited

U.S. PATENT DOCUMENTS

| | | | |
|---|---|---|---|
| 2,704,539 A | 3/1955 | Fisher | |
| 3,185,146 A | 5/1965 | Leopoldi | |
| 3,662,744 A | 5/1972 | Low et al. | |
| 4,313,446 A | 2/1982 | Kanatani | |
| 4,641,661 A | 2/1987 | Kalarickal | |
| 4,964,412 A | 10/1990 | Kelly | |
| 5,275,611 A | 1/1994 | Behl | |
| 5,316,011 A | 5/1994 | Weinstein et al. | |
| 5,381,806 A | 1/1995 | Weinstein et al. | |
| D358,169 S | 5/1995 | Osada | |
| 5,437,288 A | 8/1995 | Schwartz et al. | |
| 5,443,907 A | 8/1995 | Slaikeu et al. | |
| 5,492,132 A | 2/1996 | Weinstein et al. | |
| 5,542,434 A | 8/1996 | Imran et al. | |
| 5,562,726 A | 10/1996 | Chuter | |
| 5,582,619 A | 12/1996 | Ken | |
| 5,609,627 A | 3/1997 | Coicoechea et al. | |
| 5,680,873 A | 10/1997 | Berg et al. | |
| 5,823,969 A * | 10/1998 | Christy | 600/557 |
| 6,113,551 A | 9/2000 | Isaacs et al. | |
| D439,336 S | 3/2001 | Najimi | |
| 6,196,976 B1 | 3/2001 | Christy | |

(Continued)

OTHER PUBLICATIONS

Holewski, John J., D.P.M., Stess, Richard M., D.P.M., Graf, Peter M., D.P.M, and Grunfeld, Carl, M.D., Ph. D., "Aesthesiometry: Quantification of cutaneous pressure sensation in diabetic peripheral neuropathy," Journal of Rehabilitation Research and Development, vol. 25, No. 2, pp. 1-10, Spring 1988.

(Continued)

*Primary Examiner* — Max Hindenburg
*Assistant Examiner* — Renee Danega
(74) *Attorney, Agent, or Firm* — Convergent Law Group LLP; Rick Batt

(57) ABSTRACT

A hand held instrument for evaluation of cutaneous sensory perception includes a body member, a rotatable head, and a testing element such as a monofilament projecting from the head member wherein the head member and the body are rotatably engaged for positioning the head member with its projecting testing element at a substantially right angle from the body and for alternatively positioning the head member with its projecting testing element in a non-testing position with the testing element extending in a protected position within an elongate channel of the body. The instrument further includes a guard member or sleeve in cooperative engagement with the body and head member to cover the elongate channel in a first non-testing position and to uncover the elongate channel in a second testing position.

29 Claims, 4 Drawing Sheets

(56) References Cited

U.S. PATENT DOCUMENTS

| | | |
|---|---|---|
| 6,200,272 B1 | 3/2001 | Linden |
| 6,234,976 B1 | 5/2001 | Linden |
| 6,234,977 B1 | 5/2001 | Christy |
| D489,455 S | 5/2004 | Mork |
| 6,790,304 B2 | 9/2004 | Fox et al. |
| 8,016,769 B2 | 9/2011 | Christy |
| 2008/0097236 A1 | 4/2008 | Kuban |

OTHER PUBLICATIONS

Touch-Test.com sensory evaluators web page, Aug. 2012.
Medicalmonofilament.com web page, Aug 2012.

* cited by examiner

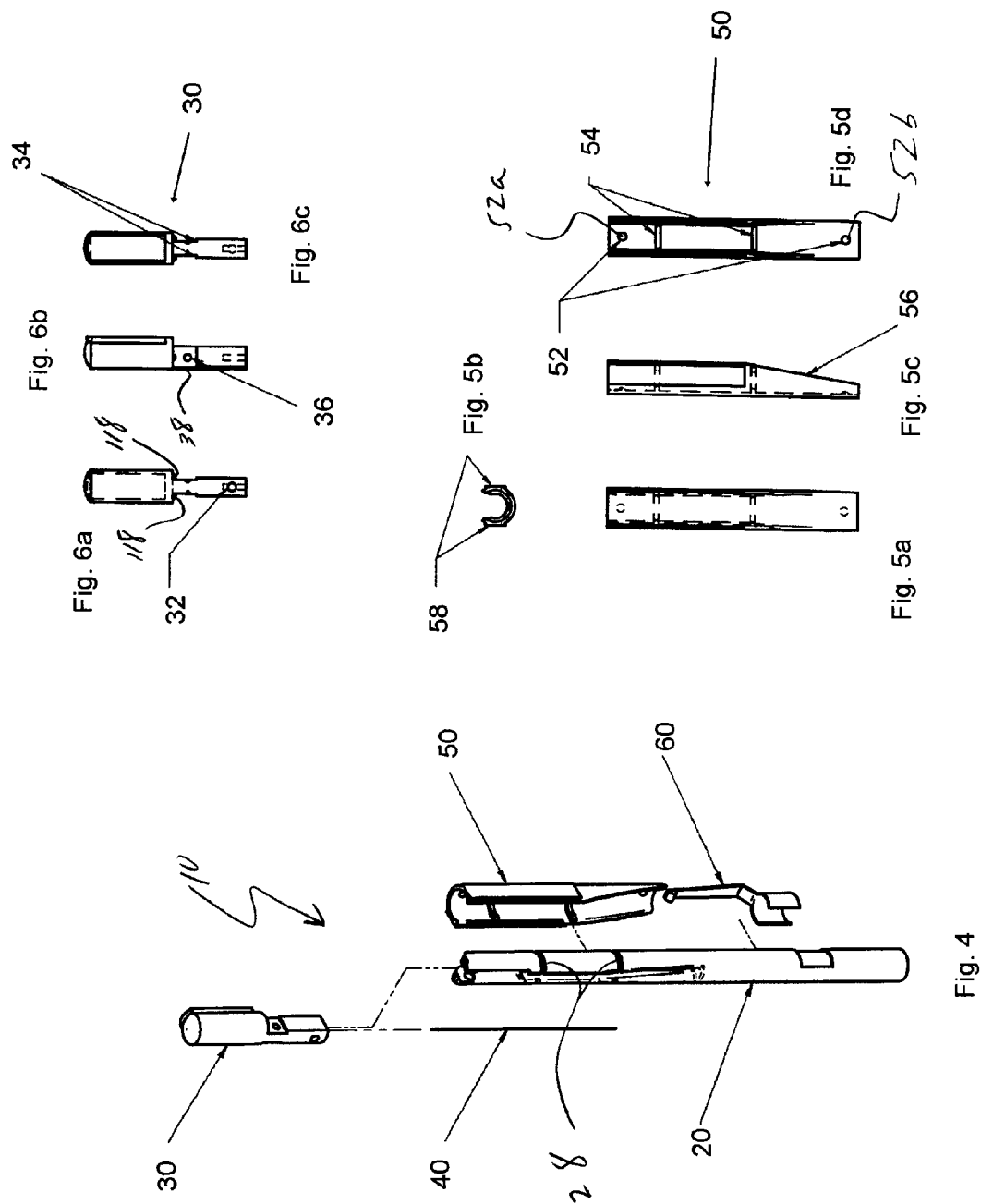

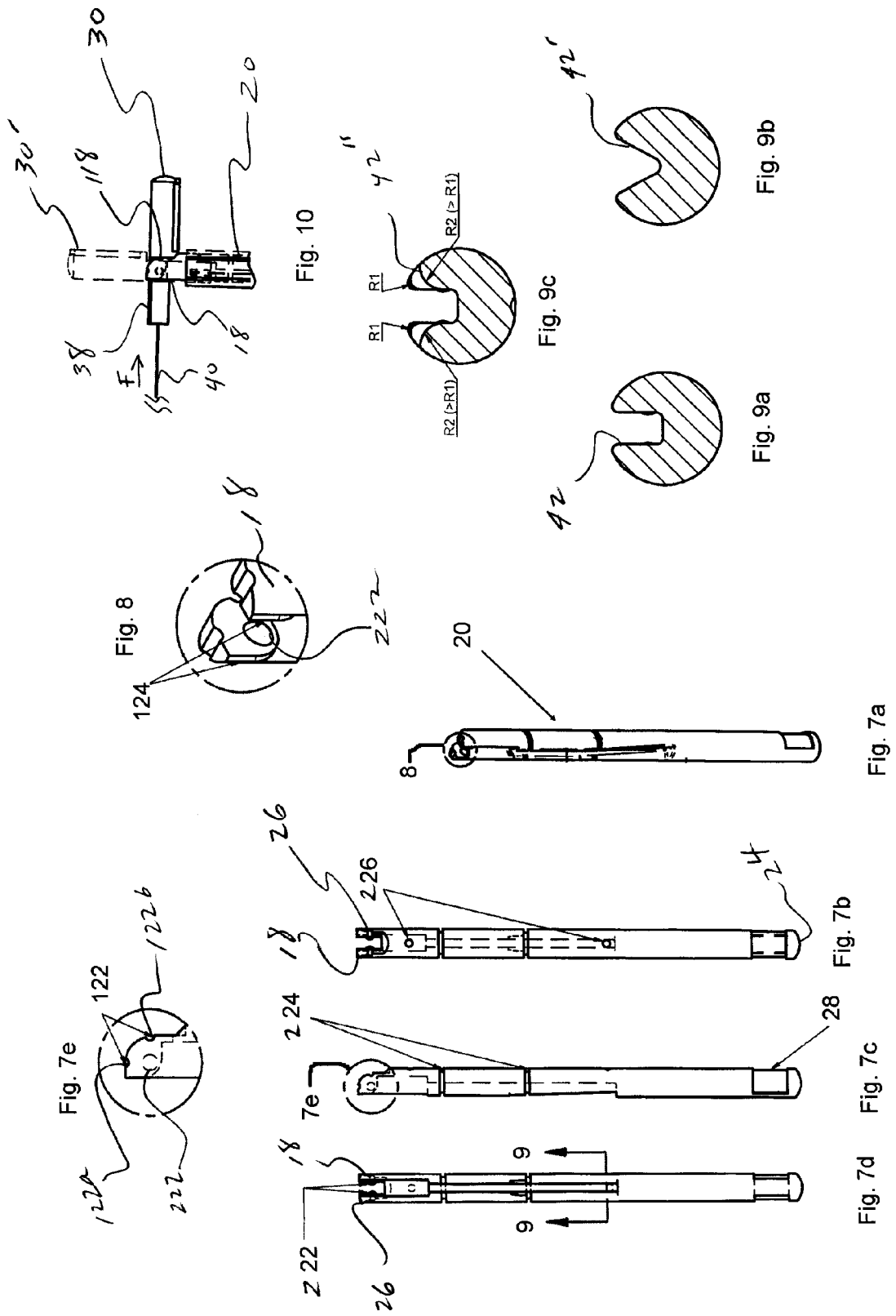

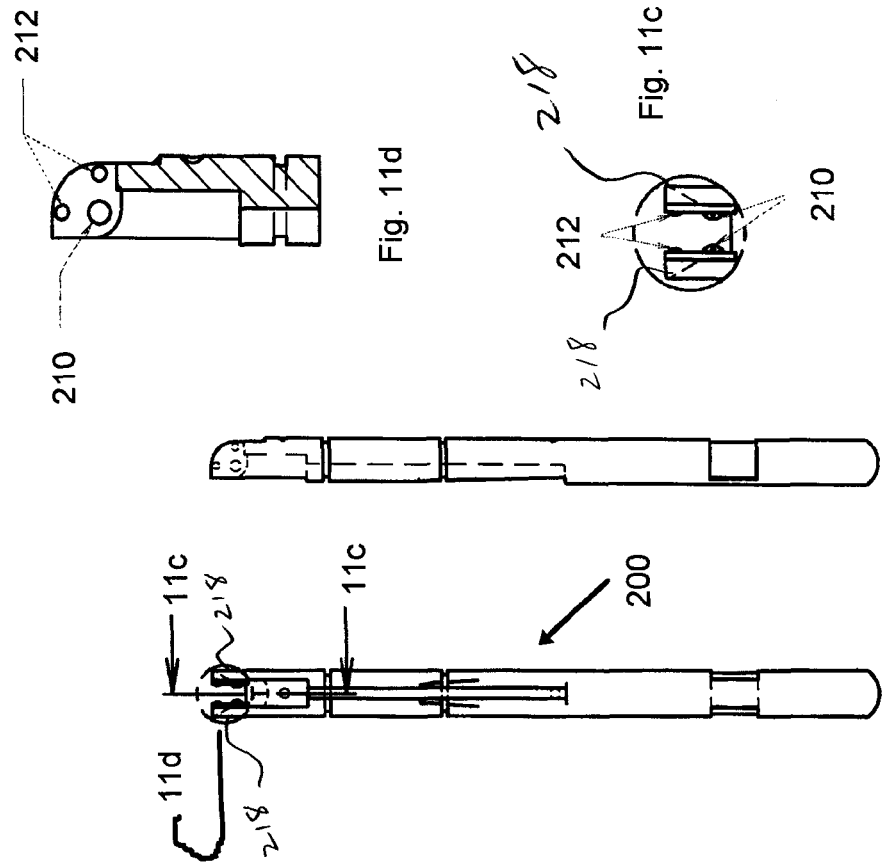

TACTILE SENSORY TESTING INSTRUMENT

FIELD OF THE INVENTION

The present invention relates generally to devices designed to test for peripheral nerve sensory function. More particularly, the invention relates to devices for testing for peripheral nerve sensory function of body surface areas of a patient using monofilaments.

BACKGROUND OF THE INVENTION

Monofilament testing for screening and monitoring of peripheral nerve function is long established. It has been shown that filaments are a sensitive monitor means for the testing of the peripheral nerve function of a patient, particularly hand and feet body areas. In the 1800's the focus of peripheral nerve testing of the hands was on the study of normal physiology and horsehairs were used as filaments to measure only light thresholds of touch recognition.

In the late 1950's it was determined that a broader range of filament forces were needed than those available with horsehairs to refine the filament method for peripheral nerve testing. J. Semmes and S. Weinstein designed and developed nylon monofilaments of increasing diameter for peripheral nerve testing with such filaments set at right angles proximate the end of acrylic (Lucite) rods. Such rods, or filament handles, are of approximate pencil length for holding and manipulation by the hand of a therapist or health care examiner measuring the peripheral nerve function of the fingers of a patient.

The Semmes-Weinstein (S-W) monofilament testing devices have become the standard means for repeatable testing and measurement of the threshold of cutaneous sensory perception. Through the 20 unit series of testing devices a trained hand therapist or health care examiner can distinguish in a patient between: light touch, diminished light touch, diminished protective sensation, loss of protective sensation, and deep pressure sensation. The series of nylon monofilaments (of uniform 38 mm length) are sized and numbered to correspond to Log(10× force in mg) of force. Lowest force in the series is 4 mg and the highest force is 447 grams. The monofilaments (of constant length, but of increasing diameters) are designed to bend when a specific value of force is reached and such design provides unique control of, and creditability to, the S-W sensory test method. Thus, the series of S-W test devices provides an accurate method by which both diminishing and returning sensation of a patient's body surfaces and extremities can be evaluated and allows the health care examiner to predict and interpret the patient's levels of nerve function and sensibility.

The well known S-W monofilament test units have been marketed as a full 20 unit series or as a set of 5 units having selected sensory level designations of 2.83, 3.61, 4.31, 4.56 and 6.65. Although the S-W monofilament test devices may be used to evaluate sensory levels of body areas and extremities of patients, they are bulky to store, carry and manipulate.

The hand held peripheral nerve function test instrument described in U.S. Pat. No. 5,823,969 to Christy (the '969 patent) addresses some of the shortcomings identified above. This instrument includes a handle of approximate pencil length and configuration with a pivotal forward head portion. A monofilament element projects from the forward head portion of the instrument for application to a body surface area for evaluating the patient's sensory perception thereof. The pivotal forward head portion of the instrument is positionable between two points of filament orientation. The first position of the head portion of the instrument results in projection of the monofilament element in a test evaluation position where the filament element extends downwardly from the handle at an angle of about 90 degrees. The second position of the head portion of the instrument results in projection of the monofilament element in a non-testing position with the filament element extending in a protected position along the length of the handle.

The '969 patent describes a number of benefits including but not limited to providing (1) a convenient shape when not in use with the monofilament elements protected from undesired bending or buckling forces, (2) an elongated handle and forward pivot head bearing the monofilament test element, and (3) an elongated handle with a two-position forward pivot head bearing the monofilament test element with the pivot head being snap-set positionable to place the monofilament element in a downwardly vertical test position at right angle orientation with respect to the handle and alternatively to place the monofilament element in a position within the handle whereby the filament element is protected from undesired bending and buckling forces during periods of non-use of the instruments.

Notwithstanding the above, various improvements to a tactile sensory testing instrument are still desired including but not limited to: (1) increased protection of the monofilament testing element when the instrument is not in use; (2) decreased static charges on the monofilament which may cause undesirable displacement or migration of the monofilament; and/or (3) a more robust pivotable joint.

Other objects and advantages of the invention will be apparent from the following summary and detailed description of the invention, taken together with the accompanying figures.

SUMMARY OF THE INVENTION

A hand held instrument for evaluation of cutaneous sensory perception includes a handle or body having a forward end and a rearward end and an elongate channel. The instrument further includes a head member rotatably affixed to the forward end of the body for rotational positioning of the head member alternatively between a testing position and a non-testing position. A testing element such as a monofilament projects from the head member wherein the head member and the body are cooperatively engaged for positioning the head member with its projecting testing element at an angle therefrom and for alternatively positioning the head member with its projecting testing element in the non-testing position with the element extending in a protected position within the elongate channel. The instrument further includes a guard member or sleeve in cooperative engagement with the body and head member to cover the elongate channel in a first non-testing position and to uncover the elongate channel in a second testing position.

In another embodiment of the present invention the head member further comprises a stop surface which serves to reduce forces on the head rotation joint structures. In one embodiment, the head member includes at least one stop and the forward end of the body comprises at least one stop surface corresponding to the stop of the head member such that when said head member is in the testing position, the head member stop is urged into contact with the body stop surface upon application of a force to the testing element. The stop surface prevents further displacement of the head member.

In another embodiment of the present invention, the elongate channel has a width, and a length, and the width increases as a function of length. In another embodiment of the present invention the width of the channel varies with the height or depth of the channel. The width may increase nonlinearly as a function of the length and/or depth. The width may increase in steps and at discrete locations along the channel. In one embodiment of the present invention, the width of the channel is greater towards the rearward end of the body of the instrument corresponding to the location of the free end of the testing element when the testing element is positioned in the elongate channel in the non-test position.

In another embodiment of the present invention a hand held instrument for evaluation of cutaneous sensory perception includes a body having a forward end and a rearward end and an elongate channel. The instrument further includes a head member rotatably affixed to the forward end of the body for rotational positioning of the head member alternatively between a testing position and a non-testing position. A testing element such as a monofilament projects from the head member wherein the head member and the body are cooperatively engaged for positioning the head member with its projecting testing element at an angle therefrom and for alternatively positioning the head member with its projecting testing element in the non-testing position with the element extending in a protected position within the elongate channel. The head member further includes a head member stop surface and the forward end of the body comprises a body member stop surface such that when the head member is in the testing evaluation position and a force is applied to the testing element the head member stop surface is urged into contact with the body member stop surface.

The instrument may further include a detachable or movable guard member to selectively cover or uncover the elongate channel.

In another embodiment of the present invention a hand held instrument for evaluation of cutaneous sensory perception includes a body having a forward end and a rearward end and an elongate channel having a width that increases as a function of length along the channel. The instrument further includes a head member rotatably affixed to the forward end of the body for rotational positioning of the head member alternatively between a testing position and a non-testing position. A testing element such as a monofilament projects from the head member wherein the head member and the body are cooperatively engaged for positioning the head member with its projecting testing element at an angle therefrom and for alternatively positioning the head member with its projecting testing element in the non-testing position with the element extending in a protected position within the elongate channel.

In another embodiment of the present invention, the channel width varies as function of depth or height. The width can increase nonlinearly as a function of the length and/or height.

In another embodiment of the present invention, the instrument comprises a guard member in cooperative engagement with the body to cover the elongate channel in a first position and to uncover the elongate channel in a second position.

In another embodiment of the present invention the head member further comprises a head member stop surface and the forward end of the body comprises a body member stop surface such that when the head member is in the testing position and a force is applied to the testing element the head member stop surface is urged into contact with the body member stop surface.

In another embodiment of the present invention the guard member or sleeve has a tapered section. The guard member may comprise a cylindrical shape and a window or opening in alternative embodiments. In one embodiment of the present invention the guard member is rotatable about the body to align the window with the elongate channel.

In another embodiment of the present invention one or more components of the instrument comprise a static dissipative material or have been treated or coated to reduce static charges.

In another embodiment of the present invention the instrument comprises a clip disposed rearward of the guard.

Any of the instruments described above may include a first head position locking feature to cooperate with a first body position locking feature of the body to lock the head in a first position preventing further rotation. In one embodiment of the present invention, the head position locking feature is at least one dimple. The body position locking features may be nipples or projections where the dimple and nipple engage together in a snap fit arrangement to lock the head relative to the body. Additionally, in another embodiment, the sleeve locking feature is at least one nipple corresponding to a body locking feature of at least one dimple, which engage together in a snap fit arrangement to lock the sleeve in the open and closed positions.

The description, objects and advantages of the present invention will become apparent from the detailed description to follow, together with the accompanying drawings.

BRIEF DESCRIPTION OF THE DRAWINGS

FIG. 4 shows an exploded view of the tactile sensing testing instrument.

FIGS. 5a-5d show various views of a sleeve member.

FIGS. 6a-6c show various views of a head member.

FIGS. 7a-7d show various views of a body member in accordance with one embodiment of the present invention.

FIG. 7e shows an enlarged view of a forward end of the body member shown in FIG. 7c.

FIG. 8 shows an enlarged view of the forward end of the body member shown in FIG. 7a.

FIG. 9a shows a cross sectional view of the elongate channel along 9-9 of FIG. 7d.

FIGS. 9b and 9c show cross sections of elongate channels of additional embodiments of the present invention.

FIG. 10 shows a partial view of body member pivotably engaged to head member in a testing and non-testing configuration.

FIGS. 11a and 11b show various views of a body member in accordance with another embodiment of the present invention.

FIG. 11c shows an enlarged view of a forward end of the body member shown in FIG. 11a.

FIG. 11d shows a cross sectional view of the forward end of the body member taken along 11c-11c of FIG. 11a.

FIG. 12 shows a partial view of body member shown in FIGS. 11a-11d pivotably engaged to a head member in a testing and non-testing configuration.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Figure 1:
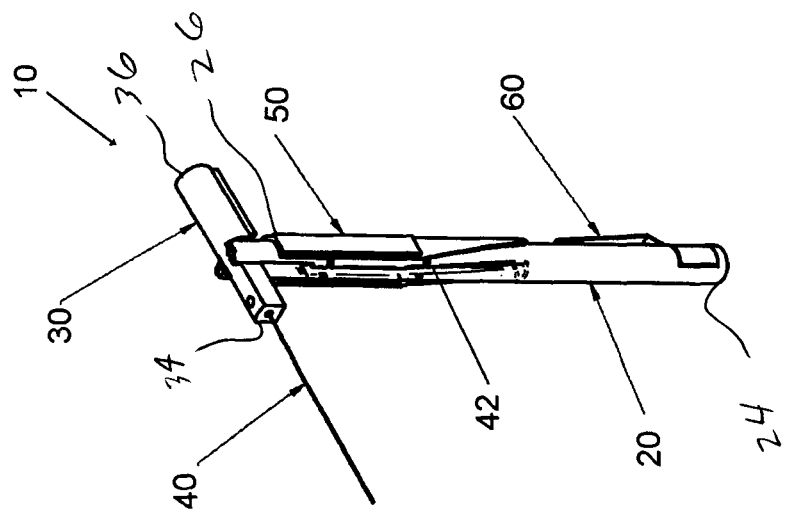
FIG. 1 shows a tactile sensing testing instrument in a testing configuration.

The present invention is directed to a manually operated tactile sensory instrument having a testing configuration and a non-testing configuration. With reference to FIG. 1, a tactile sensory testing instrument 10 in a testing position is shown. The instrument 10 is comprised of a body member 20 having a rearward end 24 and a forward end 26. As will be described in more detail in connection with FIGS. 7-10 below, a head member 30 is pivotable engaged to the forward end 26 of the body. In the testing position shown in FIG. 1, the head member forms a right angle with the body.

The instrument 10 includes a testing element 40 such as a monofilament. The testing element 40 projects from the rearward end 34 of the head member 30. The testing element 40 extends from the pivot head 30 with the axis of the element in alignment with the long axis of the head. In use, the testing element is urged against the skin of the patient to evaluate the sensory function of the patient. The properties of the testing element 40 may vary widely. The testing element may have a diameter ranging from 0.0025 to 0.050 inches and a length ranging from 1 to 2 and preferably about 1.5 inches. The resilience may also be varied. Resilience may be varied by modifying the diameter of the filament, the length of the filament, or the material of the filament. Suitable materials include, for example, Nylon, Nitinol, and spring steel.

The tactile sensory testing instrument 10 shown in FIG. 1 also includes an elongate channel 42 on a first, downward (or under) side of the body 20. The elongate channel, as will be described in more detail below in connection with FIGS. 9a-9c, is shaped to hold and protect testing element 40.

FIG. 1 also shows a guard member or sleeve 50 on a second side of the body. Guard member or sleeve 50, as will be described in more detail below in connection with FIGS. 5a-5d, may be manipulated from an open position as shown in FIG. 1 to a closed position as shown in FIG. 3 in which the sleeve 50 encloses or covers the elongate channel 42 of the body member 20.

The tactile sensory testing instrument 10 may also include a clip 60 or other fastener for engaging a surface. In FIG. 1, a pocket clip 60 is shown for engaging a pocket of a shirt of a heath care professional. Clip 60 is positioned towards the rearward end 24 of the body, allowing sleeve to be manipulated or rotated about the body 20 without interference from the clip.

Figure 2:
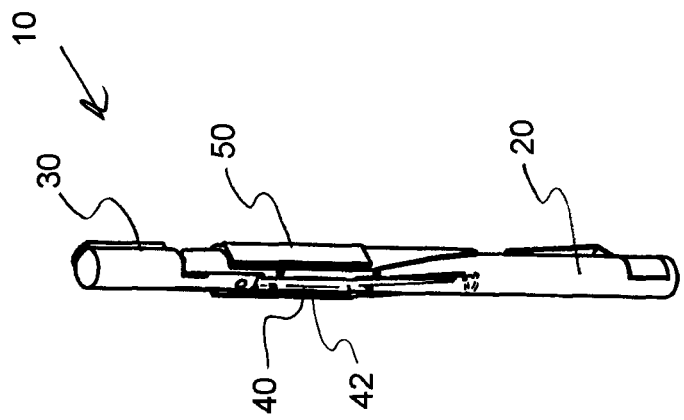
FIG. 2 shows the tactile sensing testing instrument of FIG. 1 in a non-testing position.

FIG. 2 illustrates the tactile sensory testing instrument of FIG. 1 in a non-testing position. In particular, the head member 30 is shown in line with body 20. Testing element 40 is positioned in elongate channel 42. The non-testing position shown in FIG. 2 serves to protect the testing filament and configure the instrument for convenient storage when not in use.

Figure 3:
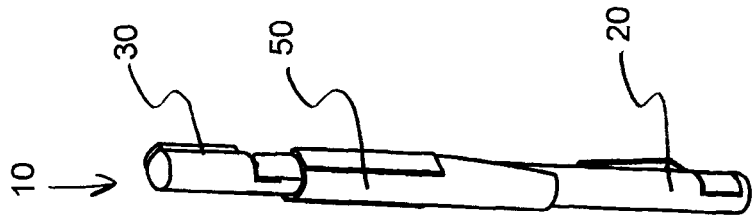
FIG. 3 shows the tactile sensing instrument shown in FIG. 2 with a guard member enclosing the testing filament.

FIG. 3 illustrates the instrument shown in the FIG. 2 with guard member 50 or sleeve covering the testing element. As indicated above, guard member 50 is movable relative to the body from a closed position in which the guard covers the channel 42, to another position (e.g., open) in which the channel is uncovered. In FIG. 3, the guard member is shown covering or enclosing the testing element. In this manner, the testing element may be protected when not in use. The testing element 40 is held within the channel by the guard, preventing the testing element from inadvertently migrating out of the channel 42.

FIG. 4 illustrates an exploded view of the tactile sensory testing instrument 10. The body member 20 is shown having two grooves 28 which engage with protrusions 54 of the sleeve shown in FIGS. 5a-5d. The grooves 28 and protrusions 54 cooperate with one another, guiding the sleeve circumferentially (rotating the sleeve) about the body member 20 from an open position to a closed non-testing position, and visa versa. Multiple grooves may be provided on the body member. The grooves may be identical or different in shape. Multiple protrusions may be provided. The protrusions may identical or different in shape.

Although grooves and protrusions are illustrated in this embodiment of the present invention, the invention is not so limited. Other means for guiding the sleeve relative to the body and head member may be adopted including but not limited to snap fit dimples, axial grooves, tethers, adhesives, pins, screws, etc. Additionally, the sleeve may be designed to make an interference or snap fit with the body member. Although the guard is preferably left on the instrument in the open, testing position, the guard member need not be. In one embodiment, the guard member is detached or removed from the body member in the testing position.

The sleeve shown in FIGS. 5a-5d includes a taper 56 which serves to facilitate entry of the monofilament into the elongate channel 42 when the sleeve is rotated from the open position to the closed position. The sleeve 50 shown in FIGS. 5a-5d also includes lock dimples or protrusions 52a,b which snap fit or register with corresponding features of the body member 20 in either the open testing position or the closed non-testing position. In a closed position, lock dimple 52a engages the sleeve lock dimple 32 of head 30 shown in FIG. 6a. In an open position, the sleeve lock dimples 52a,b engage sleeve position lock dimples 226 of body 20 shown in FIG. 7b. In this embodiment, therefore, the guard member 50 may be rotated and locked in its desired first or second position.

The sleeve 50 may have a wide variety of shapes including but not limited to a cylinder, an open semi-circular member, half-cylinder, or a cylinder comprising an opening, window, gap, slot, or aperture. The sleeve may be made from a wide variety of materials including for example, polymer such as polycarbonate, PMMA, and ABS as well as metals and alloys. Additionally, the sleeve may include a surface such as an elongated raised platform or plateau surface area upon which may be printed or etched marketing source, manufacturing or quality data, or other appropriate information. Likewise, the body and the pivot head of the instrument may also include such a surface. For example, appropriate information identifying the force rating of the monofilament element affixed to the pivot head may be printed or superimposed thereon. The sleeve may also be opaque, transparent, or translucent.

With reference to FIGS. 7a-7d, the body member 20 may be plastic (e.g., molded plastic) and in the shape of a handle. The forward end 26 of the handle 20 is shown with two integrally molded, forwardly extending handle shank portions 18. Each shank portion 18 is shown comprising a nipple or spherical protrusion 222. The shank portions 18 of the handle 20 extend forwardly in parallel orientation and straddle the rotatable, multi-position head member 30 of the instrument in its pivot arm portion 38. The nipples 222 engage the arm portion 38 of the head member 30. In particular, the nipples 222 engage or register with the dimples 36 of the head member. Alternatively, the pivot spheres may be replaced by a pivot pin extending through the pivot arm portion 38 from the straddling shank portions 18 of the handle 20.

The body member 20 shown in FIGS. 7a-7e also includes notches 122 along the shank portions 18 for engaging head-locking projections 118 of the head member 30. When the pivot head 30 is rotated to its non-operative position (non-test position) with the monofilament element positioned within protective handle groove 42 located on the underside of the handle 20, pivot head locking projections 118 (which are located on each side of the pivot head) are snap-seated into notches 122a located at the terminal end surface of the straddling shank portions 18 of the handle 20.

Although notches 122 and projections 118 are shown in FIGS. 7a-7e, the invention is not so limited. Other features may be incorporated into the instrument that serve to controllably lock the movement of the head member 30 relative to the body member 20. For example, FIGS. 11-12 illustrate another embodiment of the present invention where the shank portions 218 of the body member 200 include head locking nipples 212 that engage with corresponding locking dimples in the head member 230. Indeed, a wide variety of means may be utilized to register and lock the head member in a non-testing position and a testing position.

As indicated above, the channel or groove 42 in the handle body holds the monofilament when the instrument is in the non-testing configuration. The dimensions of the channel are suitable to fit the testing element and do not allow the testing to migrate out as the sleeve member is moved into the closed non-testing position. For example, and without limitation, the width of the channel may range from 0.06 to 0.20 inches. The length of the channel may range from 1.5 to 3 inches and more preferably range from 1.75 to 2.5 inches. It may also be desirable to have a gap or space separating the filament from the walls of the channel, and especially near the free end of the testing element.

FIGS. 9a-9c show the cross sections of a channel 42 in the body 20. FIG. 9a illustrates a square cross section. FIG. 9b illustrates a v-groove. FIG. 9c illustrates a curved varying radius cross section. Additionally, the width of the channel may vary with length. In one embodiment, the width of the channel increases along the length of the channel and in particular, the width increases non-linearly being greatest towards the rearward end 24.

The properties of the channel 42 may be modified with coatings, treatments, or additives. In one embodiment of the present invention an antistatic coating is disposed on the channel to inhibit migration of the filament when the filament is moved into the channel. Coatings, or antistatic treatments may limit the interaction of charges between the testing element and the channel or body. Additionally, or in the alternative, components of the instrument may be fabricated with materials or additives or lubricants that reduce charges or static. An example coating or additive is ammonium quaternary compounds such as Uniquat QAC80 from Lonza, Inc. An example treatment is plasma or ionizing treatment as well as vapor deposition.

The operative position of the instrument is shown in FIG. 10 with the pivot head locking projections 118 snap-seated into notches 122b located at the upper and rearward terminus of the arcuate surface of the straddling shank portions 18 of the handle 20. In the operative position (solid line of FIG. 10), the pivot arm portion 38 of the pivot head 30 is shown extending at a right angle from the instrument handle 20 whereby the monofilament test element 40, carried by the pivot arm portion 38, is oriented at an angle of 90 degrees with respect to the handle 20 and is rigidly fixed (snap-set) in such position for use in evaluating the threshold of cutaneous sensory perception of a patient's fingers and hands, or other tissue surface.

FIG. 12 shows the operative position of another embodiment of the present invention corresponding to the pivot head locking nipples and dimples described above in connection with FIGS. 11a-11d. In FIG. 12 the non-operative position of the pivot head 230 with respect to the instrument handle 200 is shown in dashed outline as pivot head member 230'.

The instrument of the present invention may also include stop surfaces which, when the instrument is in an operative testing configuration, redistribute forces arising from the procedure from the head rotation structures (e.g., head rotation dimple/nipples) to more robust stop surfaces. The stop surfaces reduce stresses and forces on the head rotation structures. Examples of the head rotation structures include head rotation dimple 36, nipple 222, 210. Examples of stop surfaces 124 are shown in FIG. 8.

In operation as shown in FIG. 10, when head member 30 is locked at a right angle as described above, and a force is applied to the testing filament 40, stop flats 34 shown in FIG. 6c, are urged against stop surfaces 124. Stop surfaces 124 of handle 20 prevent further displacement of the head member arising from the application of pressure to the filament 40. Consequently, less force is applied to the rotation structures (e.g., dimple 222 or pin not shown). The present invention thus provides stop structures in addition to the head rotation structures that make the joint more robust and reduce the likelihood of joint failure over time.

The instruments of the present invention may be provided as a plurality of instruments, set, or kit. For example, the instruments of the present invention may be provided with various monofilaments (e.g., 3-20 different filaments). The filaments may have different properties to provide a wide range of sensory testing parameters, namely, a wide range of pressures. Additionally, methods of use are intended to be within the scope of this disclosure.

It is to be understood that, although the testing instrument of the present invention has been described with respect to its use by a health care examiner for the evaluation of the threshold of cutaneous sensory perception of a patient's extremities (particularly the patient's fingers and hands and toes and feet), the tactile sensory testing instrument of the invention may be utilized for the evaluation of the threshold sensory perception of all skin surface areas of a human patient.

Further, while the invention has been described in connection with particular structural embodiments of the tactile sensory testing instrument, modifications of the monofilament element shift means for the instrument may become apparent to those skilled in the sensory testing art. Accordingly, such modifications are to be included within the spirit and scope of the invention as defined in the following claims.

We claim:

1. A hand held instrument for testing of cutaneous sensory perception comprising:
   a body having a forward end, a rearward end, a cavity, and an elongate channel extending in a rearward direction from the cavity;
   a guard member in cooperative engagement with said body to cover said elongate channel in a first position and to uncover said elongate channel in a second position;
   a head member having a forward end and a rearward end, said head member being rotatably affixed to the forward end of said body for rotational positioning of said head member alternatively between a testing position and a non-testing position; and
   a testing element affixed to and projecting from said head member wherein said head member and the forward end of said body are cooperatively engaged for positioning said head member with its projecting testing element in said testing position whereby said testing element extends downwardly from said body at an angle therefrom and for alternatively positioning said rearward end of said head member in said cavity and its projecting testing element in said non-testing position with said testing element extending in a protected position within said elongate channel.

2. The instrument of claim 1 wherein said head member further comprises at least one stop and said forward end of said body comprises at least one stop surface corresponding to said stop of said head member such that when said head member is in said testing position, said stop is urged into contact with said stop surface upon application of a force to said testing element.

3. The instrument of claim 1 wherein said channel has a width, and a length, and said width increases as a function of length.

4. The instrument of claim 3 wherein said channel further comprises a height and said width increases as a function of height.

5. The instrument of claim 3 wherein said width increases nonlinearly.

6. The instrument of claim 1 further comprising a static dissipative material.

7. The instrument of claim 1 further comprising a clip disposed rearward of said guard.

8. The instrument of claim 1 wherein said guard member comprises a cylindrical shape and a window, said guard member being rotatable about said body to align said window with said elongate groove.

9. The instrument of claim 1 wherein said head further comprises a first head position locking feature to cooperate with a first body position locking feature of the body to lock said head in a first position.

10. The instrument of claim 9 wherein said first head position locking feature is a dimple and said first body position locking feature is a nipple, and said dimple and nipple engage together in a snap fit arrangement.

11. A hand held instrument for testing of cutaneous sensory perception comprising:
   a body having a forward end, a rearward end, and an elongate channel;
   a head member having a forward end and a rearward end, said head member being rotatably affixed to the forward end of said body with cooperating pivot elements for rotational positioning of said head member alternatively between a testing position and a non-testing position; and
   a testing element affixed to and projecting from said head member wherein said head member and the forward end of said body are cooperatively engaged for positioning said head member with its projecting testing element in said testing position whereby said testing element extends downwardly from said body at an angle therefrom and for alternatively positioning said head member with its projecting testing element in said non-testing position with said element extending in a protected position within said elongate channel and wherein said head member further comprising a head member stop surface and said forward end of said body comprising a body member stop surface such that when said head member is in said testing position and a force is applied to said testing element said head member stop surface is urged into contact with said body member stop surface.

12. The instrument of claim 11 wherein said instrument further comprises a guard member in cooperative engagement with said body to cover said elongate channel in a first position and to uncover said elongate channel in a second position.

13. The instrument of claim 12 further comprising a clip disposed rearward of said guard member.

14. The instrument of claim 12 wherein said guard member comprises a tapered section.

15. The instrument of claim 11 wherein said channel has a width, and a length, and said width increases as a function of length.

16. The instrument of claim 15 wherein said width increases nonlinearly.

17. The instrument of claim 11 wherein said channel further comprises a height and said width further increases as a function of height.

18. The instrument of claim 11 further comprising a static dissipative material.

19. The instrument of claim 11 wherein said head further comprises a first head position locking feature to cooperate with a first body position locking feature of the body to lock said head in a first position.

20. The instrument of claim 19 wherein said first head position locking feature is a dimple and said first body position locking feature is a nipple, and said dimple and nipple engage together in a snap fit arrangement.

21. A hand held instrument for testing of cutaneous sensory perception comprising:
   a body having a forward end, a rearward end, a cavity disposed in the rearward end, and an elongate channel extending in the rearward direction from said cavity, said channel comprising a length, and a width, and wherein said width increases as a function of length;
   a head member having a forward end and a rearward end, said head member being rotatably affixed to the forward end of said body for rotational positioning of said head member alternatively between a testing position and a non-testing position;
   a testing element affixed to and projecting from the rearward end of the head member wherein said head member and the forward end of said body are cooperatively engaged for positioning said head member with its projecting testing element in said testing position whereby said testing element extends downwardly from said body at an angle therefrom and for alternatively positioning the rearward end in the cavity of said body, and with its projecting testing element in said non-testing position with said element extending in a protected position within said elongate channel.

22. The instrument of claim 21 wherein said channel further comprises a height and said width increases as a function of height.

23. The instrument of claim 21 wherein said width increases nonlinearly.

24. The instrument of claim 21 further comprising a guard member in cooperative engagement with said body to cover said elongate channel in a first position and to uncover said elongate channel in a second position.

25. The instrument of claim 24 further comprising a clip disposed rearward of said guard member.

26. The instrument of claim 21 further comprising a static dissipative material.

27. The instrument of claim 21 wherein said head member further comprises a head member stop surface and said forward end of said body comprising a body member stop surface such that when said head member is in said testing position and a force is applied to said testing element said head member stop surface is urged into contact with said body member stop surface.

28. The instrument of claim 21 wherein said head further comprises a first head position locking feature to cooperate with a first body position locking feature of the body to lock said head in a first position.

29. The instrument of claim 28 wherein said first head position locking feature is a dimple and said first body position locking feature is a nipple, and said dimple and nipple engage together in a snap fit arrangement.

* * * * *